United States Patent [19]

Pastrone et al.

[11] Patent Number: 5,496,273

[45] Date of Patent: Mar. 5, 1996

[54] AUTOMATED DRUG INFUSION SYSTEM WITH AUTOPRIMING

[75] Inventors: Giovanni Pastrone, Los Gatos; Noel L. Johnson, San Jose; J. Terry Huang, Sunnyvale; Timothy Allen, Mountain View, all of Calif.

[73] Assignee: Abbott Laboratories, Abbott Park, Ill.

[21] Appl. No.: 267,756

[22] Filed: Jul. 5, 1994

Related U.S. Application Data

[63] Continuation of Ser. No. 811,195, Dec. 20, 1991, abandoned.

[51] Int. Cl.$^6$ .................................................. A61M 31/00
[52] U.S. Cl. ................................................................. 604/67
[58] Field of Search ........................... 604/30–34, 49–53, 604/65, 67, 123, 153, 250–253; 128/DIG. 12, DIG. 13

[56] References Cited

U.S. PATENT DOCUMENTS

| | | | |
|---|---|---|---|
| 4,346,705 | 8/1982 | Pekkarinen et al. . | |
| 4,367,736 | 1/1983 | Gupton . | |
| 4,372,304 | 2/1983 | Avakian et al. . | |
| 4,401,432 | 8/1983 | Arp . | |
| 4,464,172 | 8/1984 | Lichtenstein . | |
| 4,479,760 | 10/1984 | Bilstad et al. ................... | 128/DIG. 12 |
| 4,525,163 | 6/1985 | Slavik et al. . | |
| 4,526,515 | 7/1985 | DeVries ................................ | 604/153 |
| 4,534,756 | 8/1985 | Nelson . | |
| 4,551,131 | 11/1985 | Miles et al. . | |
| 4,553,958 | 11/1985 | LeCocq . | |
| 4,565,500 | 1/1986 | Jeensalute et al. ..................... | 604/123 |
| 4,696,671 | 9/1987 | Epstein et al. ........................ | 604/67 |
| 4,731,051 | 3/1988 | Fischell . | |
| 4,756,706 | 7/1988 | Kerns et al. ............................ | 604/66 |
| 4,798,664 | 1/1989 | Yamaguchi et al. . | |
| 4,818,186 | 4/1989 | Pastrone et al. . | |
| 4,818,190 | 4/1989 | Pelmulder et al. ..................... | 417/360 |
| 4,821,558 | 4/1989 | Pastrone et al. . | |
| 4,828,543 | 5/1989 | Weiss et al. .............................. | 604/6 |
| 4,832,689 | 5/1989 | Mauerer et al. . | |
| 4,842,584 | 6/1989 | Pastrone . | |
| 4,846,636 | 7/1989 | Dawby et al. .......................... | 604/153 |
| 4,850,998 | 7/1989 | Schoaendorfer ......................... | 604/6 |
| 4,865,584 | 9/1989 | Epstein . | |
| 4,878,896 | 11/1989 | Garrison et al. ........................ | 604/65 |
| 4,919,596 | 4/1990 | Slate et al. .............................. | 417/18 |
| 4,927,411 | 5/1990 | Pastrone et al. . | |
| 4,950,244 | 8/1990 | Fellingham et al. . | |
| 4,995,268 | 2/1991 | Ash et al. ............................... | 604/67 |
| 5,000,739 | 3/1991 | Kulisz et al. . | |
| 5,010,473 | 4/1991 | Jacobs . | |
| 5,062,774 | 11/1991 | Kramer et al. .................. | 128/DIG. 12 |
| 5,100,380 | 3/1992 | Epstein et al. ......................... | 604/67 |

OTHER PUBLICATIONS

"LIFECARE 5000 Plum Infusion System With Concurrent Delivery Feature 2507–04–03/04" System Operating Manual, Abbott Laboratories, N. Chicago, IL, Publication #430–03388–012, Copyright 1990.

"Kinetics of Anaesthetic Drugs in Clinical Anesthesiology", *Clinical Anesthesiology International Practice And Research*, P. F. White, pp. 735, 760, 763.

"Intravenous Drug Delivery Systems", *Drug Infusions in Anesthesiology*, P. Glass et al, pp. 23 and 34.

*Primary Examiner*—C. Fred Rosenbaum
*Assistant Examiner*—Manuel Mendez
*Attorney, Agent, or Firm*—Harry G. Thibault; Thomas M. Breininger

[57] ABSTRACT

A pumping system for positive displacement, volumetric liquid control includes a pump having a pumping chamber with a pumping chamber inlet and a pumping chamber outlet. The pumping system further includes a liquid supply inlet for receiving liquid from a liquid supply, and an detector for detecting air in liquid flowing through the liquid path. A liquid valve actuator regulates liquid flow through the liquid supply inlet and a second valve actuator regulates liquid flow through the pumping system outlet. A controller is responsive to an output from the detector to control the pump, the first valve actuator and the second valve actuator such that liquid is directed through the liquid supply inlet and the pumping system outlet during an initial priming sequence until the quantity of air in liquid at the pumping system outlet corresponds to a predetermined value.

27 Claims, 5 Drawing Sheets

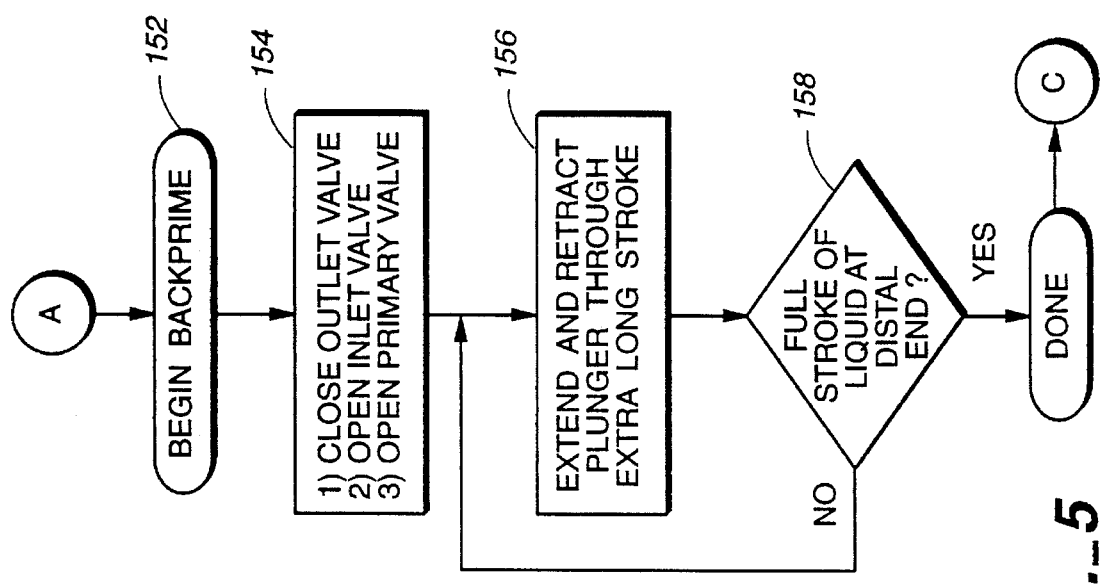
FIG._5
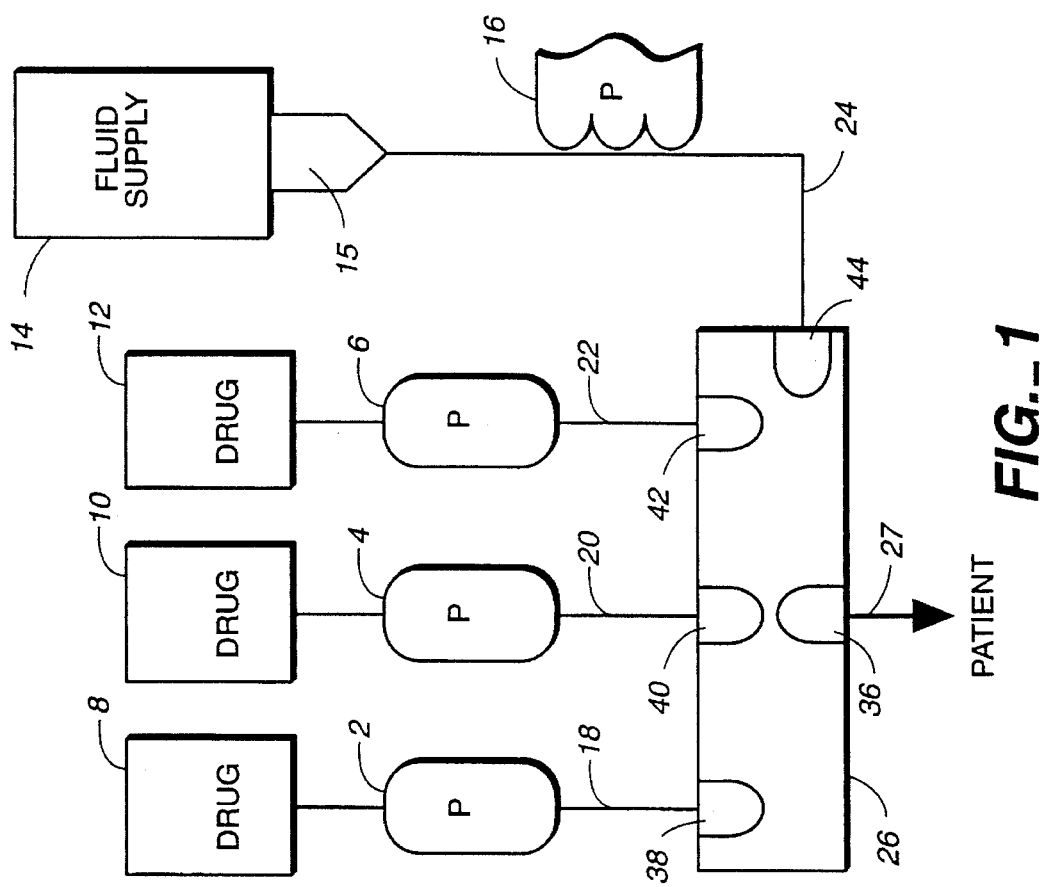
FIG._1

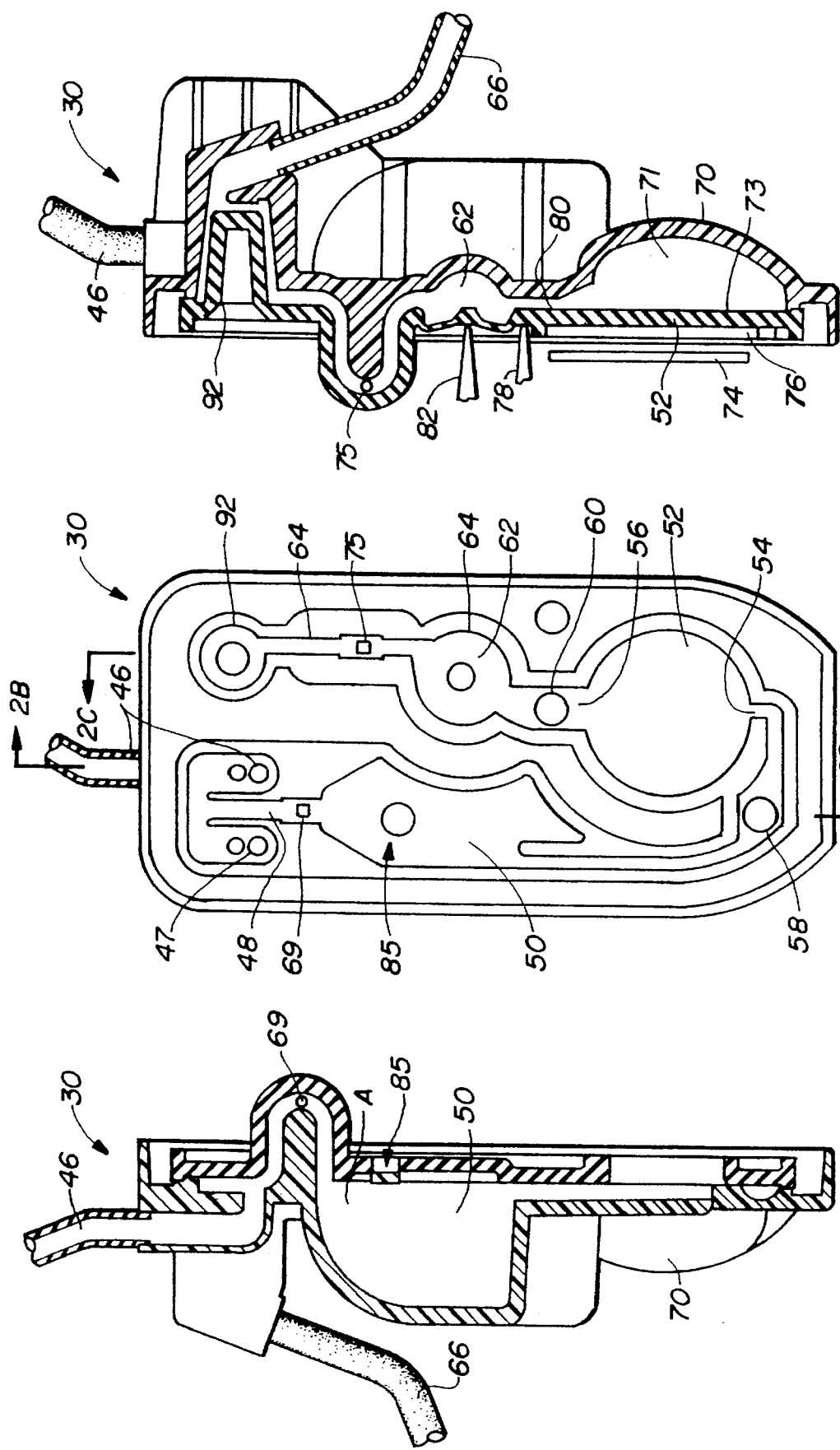

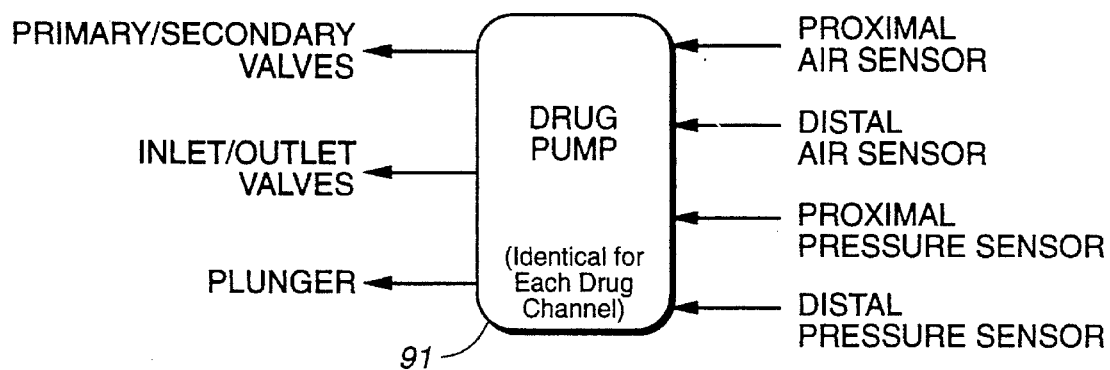
FIG._3A
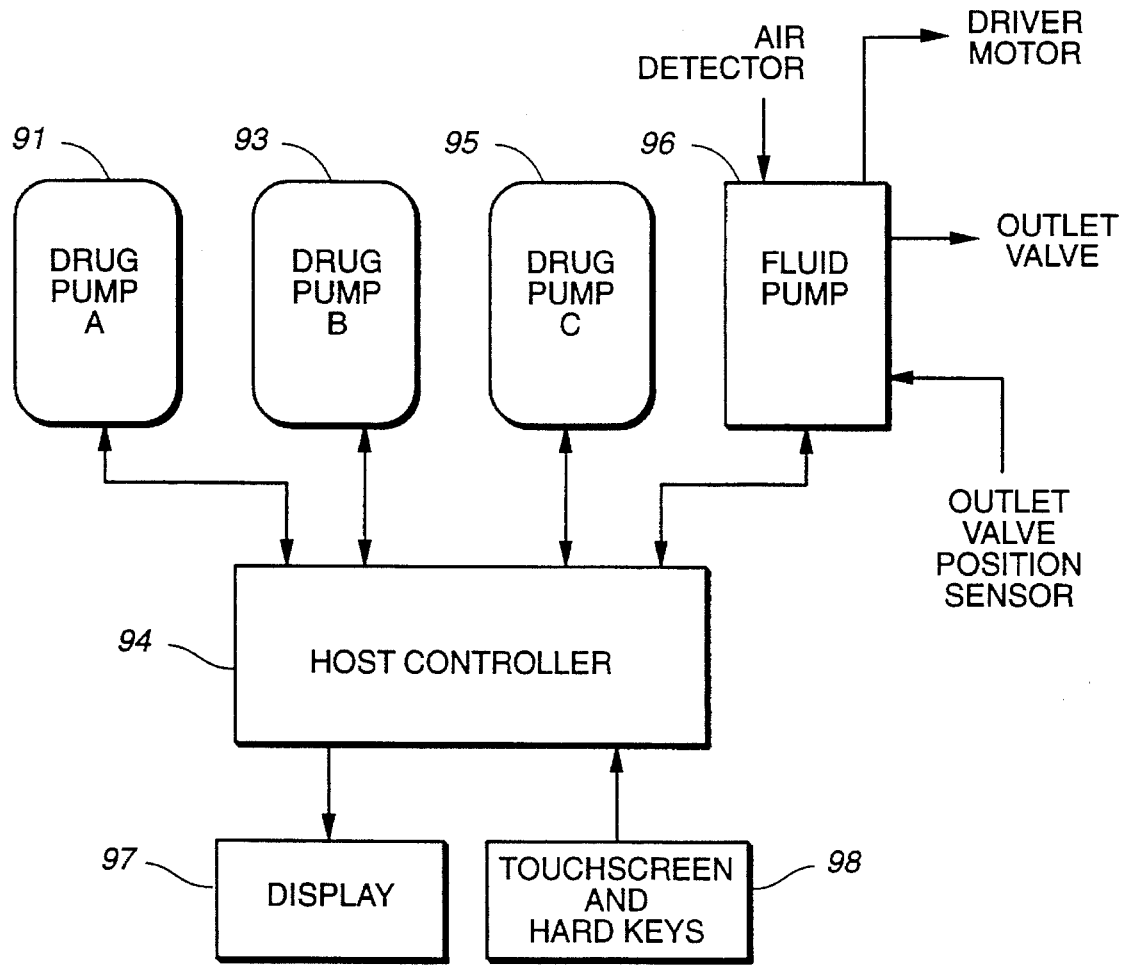
FIG._3

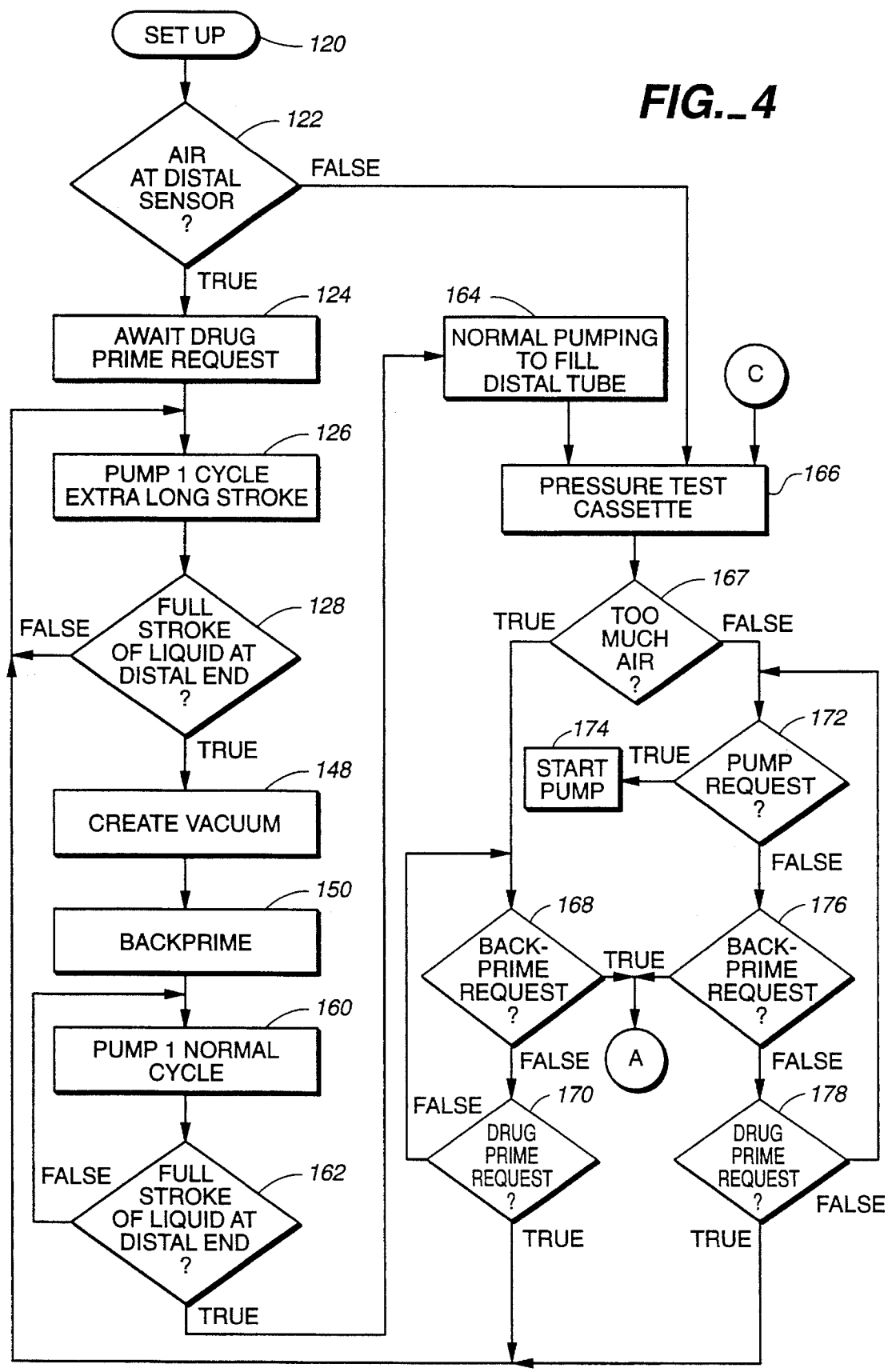
FIG._4

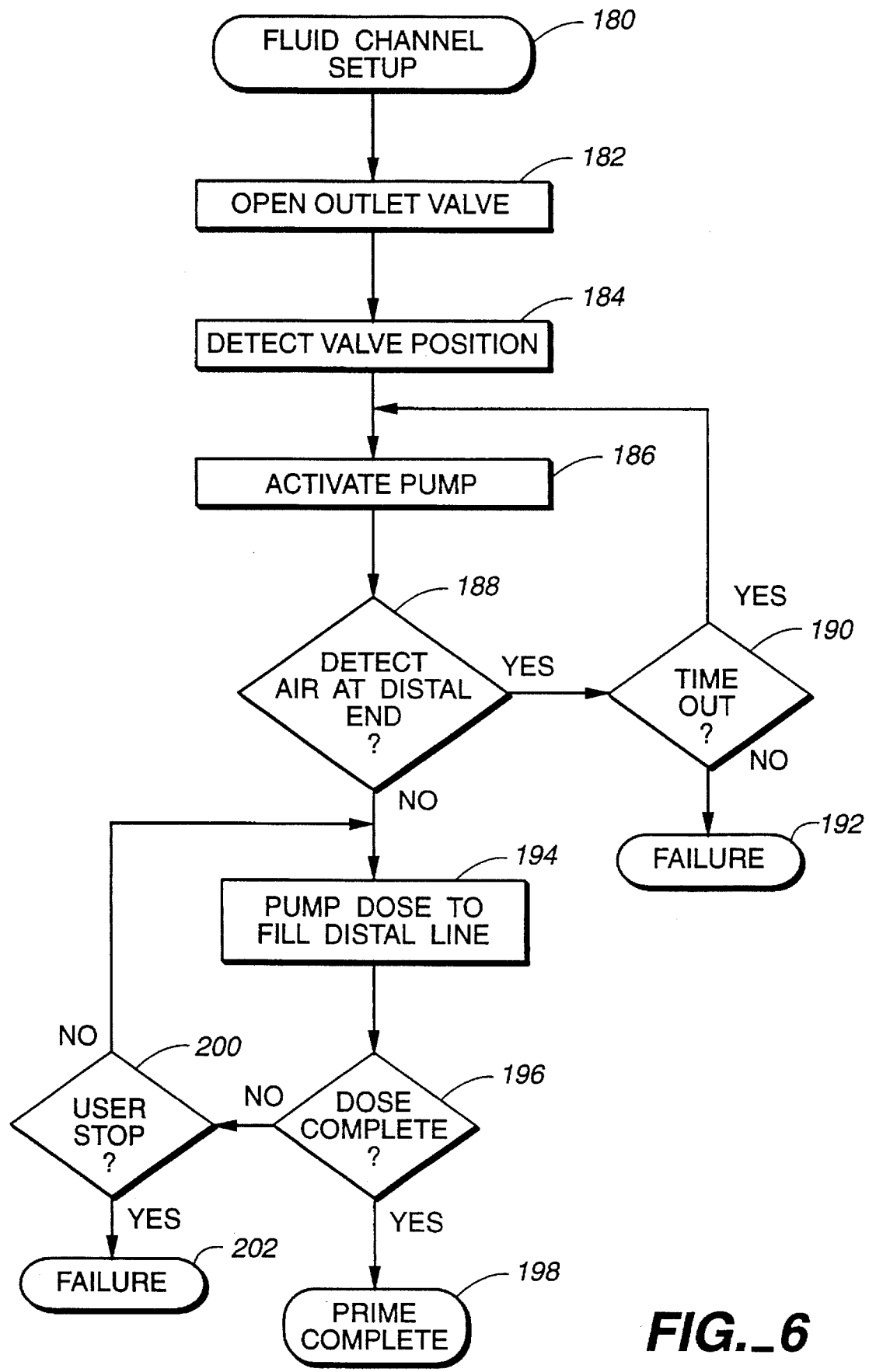
FIG._6

AUTOMATED DRUG INFUSION SYSTEM WITH AUTOPRIMING

This application is a continuation, of Application Ser. No. 07/811,195, filed Dec. 20, 1991 and now abandoned.

BACKGROUND OF THE INVENTION

1. Field of the Invention

The present invention generally relates to systems for delivering drugs to patients intravenously. More particularly, the present invention relates to positive-displacement volumetric infusion pumping systems.

2. State of the Art

It is well known to use positive-displacement volumetric infusion pumping systems for delivering drugs to patients intravenously. Infusion pumping systems of conventional design, however, have the shortcoming that manual priming is required whenever a drug supply container is connected or replaced in the pumping system. The manual priming procedures are time consuming and labor-intensive; accordingly, such procedures are costly, especially when performed by trained nurses or physicians.

SUMMARY OF THE INVENTION

Generally speaking, the present invention provides an automated priming system for positive-displacement, volumetric infusion pumping systems of the type that are designed for dispensing drugs to a patient intravenously from one or more drug supply containers. The drugs normally are in liquid form or are dissolved in liquid carriers.

For purposes of the following discussion, the term "drug channel" refers to a path through which drug is dispensed to a patient from at least one drug supply container or vial. In systems according to the present invention, a drug channel includes a cassette pumping device and at least one air sensor in the path between the drug supply inlet and the pumping system outlet for detecting air in the drug path. A first valve actuator regulates flow into the pumping chamber and a second valve actuator regulates flow from the pumping chamber outlet. A controller is responsive to an output from the air sensor to control the pump, the first valve actuator and the second valve actuator during an initial priming sequence until all air is removed from drug present at the pumping system outlet.

In an exemplary embodiment, automated priming of the aforementioned pumping system is effected in response to keyed activation by a user. Air is automatically removed from the pump while filling the pump with a drug prior to initiation of an infusion cycle. The present invention thus provides easy to use methods and systems which improve patient care by enhancing drug delivery and by reducing contamination due to manual handling of the priming sequence.

In a preferred embodiment, the automated priming includes a backpriming sequence. The term "back-priming" refers to dispelling drug and air from the cassette toward the drug vial, with the result that air entrapped in the drug is released into the drug vial.

BRIEF DESCRIPTION OF THE DRAWINGS

The present invention can be further understood with reference to the following description and the appended drawings, wherein like elements are provided with the same reference numerals. In the drawings:

FIG. 1 is a schematic diagram that generally shows an automated drug infusion (ADI) pumping system of the type that dispense drugs to a patient intravenously from one or more drug supply containers, all according to the present invention;

FIG. 2A is a front view, partially cut away, of a drug channel pumping cassette for automated priming according to the present invention;

FIGS. 2B and 2C are cross-sectional views of the drug channel pumping cassette of FIG. 2A, which views are taken along the lines 2B—2B and 2C—2C, respectively;

FIGS. 3 and 3A are functional block diagrams of an automated priming system for volumetric infusion pumping systems of the type that dispense drugs to a patient intravenously from one or more drug supply containers;

FIG. 4 is a process flow chart showing a drug channel priming sequence for the system of FIG. 1;

FIG. 5 is a process flow chart showing a back-priming sequence for the system of FIG. 1; and FIG. 6 is a process flow chart showing a fluid channel priming sequence for the system of FIG. 1.

DETAILED DESCRIPTION OF THE PREFERRED EMBODIMENTS

The automated drug infusion (ADI) pumping system in FIG. 1 includes three drug channels 18, 20 and 22 for dispensing drugs from vials 8, 10 and 12, respectively. The drug channels further include pumps 2, 4 and 6, respectively. At the pump outlets, the drug channels 18, 20, 22 connect to a manifold 26 via one-way check valves 38, 40, and 42, respectively. The manifold 26 connects to an outlet line 27 through which drug, or drug mixtures, are dispensed to a patient intravenously.

As also shown in FIG. 1, the automated drug infusion pumping system includes a channel 24 for carrying fluid such as a patient hydration solution or a flushing solution. The fluid channel 24 includes a fluid supply container 14 which is connected to a conventional drop sensor 15. The drop sensor is connected to fluid conduit (e.g., plastic tubing) that passes through a volumetric fluid channel pump 16. In the illustrated embodiment, the fluid channel connects to the manifold 26 via a one-way check valve 44.

Each of the pumps 2, 4 and 6 includes a mechanical reciprocating plunger mechanism and a pumping cassette through which the drugs are pumped. A representative one of the pumping cassettes, generally designated by the number 30, is shown in FIGS. 2A–2C.

In the illustrated embodiment, the pumping cassette 30 has a primary inlet port 46 and a pumped-liquid outlet port 66. The primary inlet port 46 is connected to one of the drug channels (e.g., channel 18) for receiving drug from a vial. However, alternative drug containers can be used in the system of the present invention. In the illustrated embodiment, the cassette also includes a secondary inlet port 47 which remains normally closed. However, if desired, the secondary inlet port can receive a second drug, or drug diluent, for mixing with drug which has been introduced to the cassette via the primary inlet port 46.

The pumping cassette 30 further includes an inlet channel 48 for conveying drug from the primary inlet port 46 to a reservoir 50 which functions to trap air before it can reach other areas of the cassette. In practice, the volume of the reservoir 50 is approximately 1 ml. A proximal air detector 69 is mounted for detecting air bubbles that are carried by drug flowing through the inlet channel 48. In practice, the proximal air detector 69 is a conventional ultrasonic detector.

As also shown in FIGS. 2A and 2B, a proximal pressure detector port 85 is provided for receiving a detector. The proximal pressure detector senses fluid pressure within the reservoir 50. In practice, the proximal pressure detector is a conventional strain gauge.

Further in the pumping cassette 30, a flow channel 54 leads from reservoir 50 into a pumping chamber 52, and a flow channel 56 leads from the pumping chamber 52. At the inlet to the pumping chamber 52 is an inlet valve 58 for selectively stopping liquid flow. Likewise, at the outlet of the pumping chamber 52, there is an outlet valve 60. The valves 58, 60 normally are conventional devices. For example, each of the valves can include a pin member (e.g., outlet valve pin 78 in FIG. 2C), an elastomeric member (e.g., portion of elastomeric member 73), an associated valve seat for receiving a rounded end of the pin member, and an actuator mechanism for selectively urging the pin member to press the elastomeric member into the valve seat for blocking flow.

One wall 70 of the pumping chamber 52, as best shown in FIG. 2C, provides a bulb-like recess 71. The opposite wall 73 comprises an elastomeric member. A reciprocating plunger mechanism 74, mentioned above, is connected for selectively working the elastomeric member 73 back-and-forth into the bulb-like recess. As the elastomeric member 73 is worked, it draws drug into the reservoir and pumping chamber and then ejects drug from the pumping chamber.

As further shown in FIGS. 2A and 2C, the flow channel 56 connects the pumping chamber 52 to a distal pressure detector which includes a pressure detection chamber 62. A distal pressure detector port 64 communicates with the distal pressure detection chamber 62. In practice, the port 64 receives a distal pressure transducer which, is, for example, a strain gauge like the proximal pressure detector. The strain gauge is generally represented as a pressure detector pin 82 which detects variations in a portion of the elastomeric member 73 associated with the pressure detection chamber 62.

Following the pressure detection chamber 62 is a distal air detector 75 which is mounted for sensing air bubbles that are carried by drug flowing past the distal pressure detection chamber 62. In practice, the distal air detector 75 is an ultrasonic sensor like the proximal air sensor.

Finally, as shown in FIGS. 2A and 2C, a pressure regulator 92 is mounted between the distal detector and the outlet port 66. In practice, the regulator 92 is needle valve that can be manually adjusted to determine the volumetric flow through the cassette.

FIG. 3 shows a system, including a host controller represented as processor 94, for simultaneously controlling each of the FIG. 1 drug channels. More particularly, for each cassette in each drug channel, the controller 94 operates one of the plunger mechanisms 74 by driving a motor of a pump module. The motors used to drive the plunger mechanism for each of the FIG. 1 system cassettes are included in each of the drug pumps modules 91, 93 and 95, as well as the fluid pump module 96 of FIG. 3. The controller also operates valve actuators for each of the FIG. 1 drug channel cassettes as represented generally in FIG. 3. The controller 94 receives input signals from the distal and proximal air detectors represented generally and from the distal and proximal pressure detectors represented generally in FIG. 3.

As further shown in FIG. 3, the controller 94 is connected to a display device 97 and to a touch screen and keyboard 98.

The display device can comprise, for example, an LCD display or an LED display. The touch screen 98 allows a user to provide commands, such as priming start signals, to the controller 94.

For each pumping cassette, the controller 94 responds to outputs from the two air detectors (i.e., proximal and distal air detectors 69, 75), the two pressure detectors, (i.e., proximal pressure detector at port 85 and distal pressure detection chamber 62), and the user commands to control bi-directional flow within the drug channels. As will be discussed below in detail, bi-directional flow control is critical for autopriming. During autopriming, the controller 94 operates the valve actuators and plungers in each drug channel to displace air from the drug channel. Further, the autopriming sequence can be used for priming the output line from the manifold 26 to a catheter.

Operation of the autopriming system will now be described in conjunction with FIG. 4. After proper setup of the system, autopriming of any one (or all) of the drug channels can be initiated in response to a single autopriming command for each drug channel. Preferably, each drug channel operates independently and, therefore, the system can prime two or more drug channels at the same time.

Drug Channel Setup

As indicated at block 120 in FIG. 4, autopriming begins by setting up at least one of the drug channels. To set up a drug channel, a user spikes a cassette into a drug vial, or other drug container, and then mounts the cassette to a cassette pump. In practice, a switch is closed when the cassette is connected to a cassette pump, thereby initiating an air check (block 122) at the distal air detector. That is, the presence of drug at the cassette outlet is detected by the distal air detector.

A positive response to the air check at the distal air detector will occur, for instance, when a new cassette is placed in the channel. However, a positive response from the distal air detector usually does not occur when a user is merely replacing an empty drug vial. During a distal air check of a given drug channel, the display 97 (FIG. 3) prompts the user to verify and confirm that the drug vial in the channel is not empty and that the system is ready to start autopriming.

To initiate an autopriming sequence, a user provides a request, as represented by block 124, for priming the cassette with a drug from a drug vial.

Drug Channel Autopriming Sequence

At the start of an autopriming sequence, the controller 94 prompts the user to ensure that outlet tubing from the manifold is not connected to a patient. (Similarly, the controller prompts the user to confirm that the tubing has been reconnected to the patient upon completion of an autopriming sequence.) Upon receiving an autoprime request, the controller 94 commands an autoprime of a drug pump module associated with one of the pumping cassettes. Normal air and pressure sensing alarms are disengaged during an autopriming sequence. Each drug pump module contains a controller which interfaces to the sensors and motors of that drug channel and performs the detailed functions of the autopriming process.

To execute an autopriming sequence in a selected drug channel, the pumping cycle of the reciprocating plunger mechanism for the drug pump in the channel is controlled upon confirmation by the user that pumping should be initiated. In practice, the pumping cycle under such circumstance is characterized by extra-long pumping strokes. The extra-long pumping strokes are employed for quickly filling the pumping chamber 52 with drug from the drug vial. As indicated by blocks 126 and 128 in FIG. 4, the extra-long pumping strokes are repeated until the pumping chamber is completely filled with drug. This will occur typically after two extra-long cycles.

A pumping cycle, as referred to above, includes the following steps which are described with respect to the FIG. 2A cassette: (1) closing the pumping chamber outlet valve 60, opening the chamber inlet valve 58, and retracting the plunger mechanism 74 (FIG. 2C) away from the cassette to draw drug into the pumping chamber 52 from reservoir 50; and then (2) closing the pumping chamber inlet valve 58, opening the pumping chamber outlet valve 60, and extending the plunger to push drug from the pumping chamber 52 to the cassette outlet 66. In practice, about 0.33 ml of drug is pumped per normal stroke of the plunger mechanism.

In practice, the tubing used to transfer drug from the cassette to a patient has a volume of 1.42 ml and the volume of the FIG. 1 manifold 26 is about 0.25 ml. Thus, the total volume of a drug channel is approximately four (4) ml. In practice, an extra long stroke of the plunger mechanism 74 displaces about 0.46 ml.

The condition of the pumping chamber 52 being completely full of drug can be detected by monitoring the flow of drug out the distal end of the cassette. Due to the drug flow path volumes for the pumping cassette, once the pumping chamber has been filled once, it will always be full during subsequent pumping cycles until the drug supply is depleted. Therefore, once a complete stroke of only drug (no air bubbles) is seen at the distal end of the cassette, the condition of having a full pumping chamber is guaranteed. Further, due to the physical, upright orientation of the pumping chamber (as shown in FIG. 2) and the fluid path distal to it, any air in the pumping chamber would be discharged during the initial portion of the plunger extension. A drug filled condition of the pumping chamber 52 is thereby detected by monitoring air during an initial part of the plunger extension. It will be appreciated that this method reduces the quantity of wasted drug during the priming sequence.

It should be understood that, even after the pumping chamber 52 has been initially filled with liquid, a significant quantity of air can be entrapped in the cassette. In the above-described system, the trapped air is localized to the reservoir 50 which functions as an air-trap chamber. The process of removing air from the reservoir in this condition is indicated in FIG. 4 as a two step process of creating a vacuum (i.e., negative pressure) in the air-trap (block 148), and then back-priming (block 150). In an alternate embodiment, the creation of negative pressure in the reservoir can be eliminated if the reservoir is small enough that back-priming alone can remove all of the air.

The process of creating a vacuum within the cassette will be described with respect to the cassette illustrated in FIGS. 2A–2C. For the cassette 30 of FIGS. 2A–2C, negative pressure is created in the reservoir 50 by closing the cassette primary inlet port 46 and secondary inlet port 47, and then executing one or more pumping cycles to force drug from chamber 52 toward the cassette outlet port 66. As this liquid is expelled, the volume of air in the cassette must expand to fill the volume removed as liquid. This resulting gas volume expansion is directly proportional to a pressure reduction as dictated by the ideal gas law. After negative pressure is created in reservoir 50, the primary inlet valve 46 is opened. This allows drug to rush from the drug vial into the reservoir 50.

At this point, there will still be some air resident in the air-trap reservoir 50. This volume of air can be removed by the aforementioned back-priming process. During back-priming, drug and air are dispelled from a cassette toward the associated drug vial, with the result that air entrapped in the drug is released into the drug vial. FIG. 5 shows the steps for executing a back-priming sequence.

Back-priming begins by closing the Figure 2A pumping chamber outlet valve 60, opening the pumping chamber inlet valve 58, and opening the primary inlet port 46 (blocks 152 and 154 in Figure 5). Then, extra-long pumping strokes of plunger mechanism 74 are initiated (block 156) to back-prime the drug channel by pushing air and drug from the reservoir 50 back toward the drug vial; that is, a drug/air mixture is pumped from the cassette into the drug vial where air is released. Thereafter, drug from the drug vial is drawn back into the reservoir 50 with each intake stroke of the pumping cycle. The valves remain in the positions set at block 154 until no air is sensed by the proximal detector during an entire pump stroke (block 158).

To successfully execute the above-described back-priming sequence, the volume of the pumping chamber 52 must have a certain relationship relative to the drug path volume. Typically, the volume of the path from a drug vial to the top of the reservoir 50 (i.e., point "A" in FIG. 2B) is no greater than about 0.3 ml. As mentioned above, a extra-long stroke of the plunger mechanism 74 displaces about 0.46 ml. Accordingly, during back-priming, a full stroke of the plunger mechanism 74 displaces the uppermost 0.16 ml volume of the reservoir back into the drug vial.

When an unacceptable quantity of air is detected by the proximal air detector during a complete stroke of plunger 74, the back-priming sequence is discontinued and pumping from the primary inlet port toward the cassette outlet is initiated (block 160 of FIG. 4). During pumping, the distal air detector 75 is monitored (block 162). When an unacceptable quantity of air is no longer detected, priming of the cassette is complete. Normally, only one successful pumping cycle need be counted for autopriming of the drug channel pump to be considered complete. Under normal conditions, less than about thirty seconds is required for autopriming a drug channel cassette.

After an autopriming sequence is completed, normal pumping is used for priming the distal tubing that extends between the pumping cassette and the manifold. The information on how much to prime is preset in the host controller 94. When the initial command to prime is given to a drug pump, this volume is transmitted from the host controller to the drug pump at that time. A dosage limit might be, for example, 1.5 ml for a 60-inch administration set with 0.041 inch inner diameter tubing.

After priming the distal tubing, a cassette pressure test, as indicated by block 166 in FIG. 4, is performed by the proximal and distal pressure detectors. This test verifies that no significant quantity of air remains in the cassette. During this test, the primary and secondary inlet ports and the cassette outlet valve are closed and the pumping chamber 52 and reservoir 50 are pressurized. Since air is compressible and liquids are not, the quantity of pressure increase detected at the proximal pressure detector indicates how much air remains in the cassette. If too much air is resident in the cassette at this point, the drug pump will not allow normal pumping.

In practice, this pressure test is performed whenever an autoprime or back-prime is complete, or when a fluid filled cassette is inserted into a drug channel. In this manner, the system is capable of determining if a previously primed cassette which is removed from, and then re-introduced into a drug channel is still adequately primed. By this method, the need to re-prime an already primed cassette is avoided.

As indicated in FIG. 4, determining if a newly introduced cassette is primed is a two step process. The first step is an examination of the distal air sensor (block 122). For a never-primed cassette, there will be air at the distal sensor, and the autopriming process as described above can be exploited as indicated by the TRUE decision path of block 122. However, if the cassette had been previously primed, then drug will be detected at the distal sensor. As mentioned above, the cassette pressure test (block 166) will be executed when a previously primed cassette is introduced as indicated by the FALSE decision path of block 122. If the cassette is still adequately primed, the condition of too much air (block 167) will be FALSE, and the controller will allow the user to select pumping (block 172), back-priming (block 176), or autopriming (block 178). However, if the system determines that the pressure in the cassette is inadequate indicating that there is too much air (i.e., decision block 167 is TRUE), the user is only allowed to back-prime (block 168), or autoprime (block 170).

As indicated in the above paragraph, the processing of a back-prime sequence can be commanded in a manner similar to that of a complete autoprime. This would be useful in the condition where a previously primed cassette has air in the reservoir 50 only. In this case, the cassette pressure test would indicate that there was too much air (block 167 of FIG. 4), and the user could choose to initiate a back-prime to push the air into the drug supply vial. In this condition, a backprime would be performed as described above and would be complete when a full stroke of drug is seen to be expelled into the proximal supply (block 158 of FIG. 5). Typically, the cassette pressure test would be successful upon completion of this back-priming and pumping would be allowed. However, if the air is trapped in the pumping chamber 52, then the back-prime would not remove this air and the user would have to request a complete autoprime (block 170 of FIG. 4) to remove the air.

Upon completion of the autopriming sequence, the user is requested to confirm that priming has been completed. Afterwards, all normal air and pressure sensing alarms are reactivated.

Fluid Channel Autopriming

As shown in FIG. 6, the fluid channel autopriming sequence begins with the step of setting up the fluid channel (block 180). Then, following a user's command, the steps in the autopriming sequence include:

(a) opening the volumetric pump outlet valve (block 182);

(b) detecting the valve position through an optical sensor (block 184); and, (c) initiating normal pumping strokes of the volumetric pump (block 186) at a predetermined rate.

In normal operation of an ADI system, as a safety feature, the outlet valve from the pumping chamber is designed to open when pressure in the chamber exceeds a predetermined threshold. This prevents air from being delivered in a pumping line to a patient. During an autopriming sequence, however, it is necessary to pump air out the distal end of the tubing. Therefore, this outlet valve is forced open by a separately driven valve motor during autopriming so that air can be pumped. The processing indicated in the autopriming sequence steps (a) and (b) above performs this act of enabling the ability to pump air.

During the fluid channel autopriming sequence, the distal detector status is monitored. Pumping continues until continuous fluid flow is detected at the distal end of the fluid pump (block 188) or failure is detected by a time-out (block 190).

When the detector senses that the air present at the pump outlet is less than the predetermined value, the outlet valve is closed. If a failure condition occurs (e.g., time-out), the pump is stopped and an alarm state is indicated (block 192). Other detectable failures include proximal or distal occlusions; these conditions can be detected, for example, by pressure increases in the pump or by the absence of fluid at the pump inlet or outlet. The absence of fluid at the pump outlet can be sensed by a distal detector.

If the detected quantity of air in the fluid is above the predetermined limit, the controller provides rate, volume (dosage limit) and priming commands to the fluid pump based on information previously provided by the user. Then, fluid is delivered at the pre-selected rate and dosage for a period sufficiently long to fill the tubing all the way to the manifold (blocks 194, 196). When the dosage limit is reached, the pump discontinues pumping and the display indicates that autopriming of the fluid channel has been completed (block 198).

A user may send a stop command to abort priming of the fluid channel at any time by entering an appropriate command on the controller touch screen (e.g., blocks 200, 202). In practice, an autopriming sequence can be interrupted and later resumed with a partially-filled volumetric pump 18 (FIG. 1) or initiated with a partially filled volumetric pump 18.

It will be appreciated by those skilled in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A pumping system for providing positive displacement, volumetric liquid control comprising:

a liquid supply channel having a liquid supply inlet for receiving liquid from a liquid supply;

a pump included in said liquid supply channel and having a pumping chamber with a pumping chamber inlet and a pumping chamber outlet;

at least one detector, located in said liquid supply channel between the liquid supply inlet and a pumping system outlet, for detecting air in liquid flowing through the liquid supply channel;

a first valve and valve actuator for regulating liquid flow through the liquid supply inlet and a second valve and valve actuator for regulating liquid flow through the pumping system outlet; and a controller responsive to an output from the detector for controlling the pump, the first valve actuator and the second valve actuator during a bi-directional priming of the liquid supply channel until a quantity of air in liquid within the liquid supply channel corresponds to a predetermined value.

2. A pumping system according to claim 1, further comprising:

at least one additional detector located between the pumping chamber outlet and the pumping system outlet for detecting air in the liquid supply channel.

3. A pumping system according to claim 2, further comprising:

means to input liquid supply control data to the controller; and a display for displaying a status of the pumping system.

4. A pumping system according to claim 2, further comprising:

at least one pressure detector in the liquid supply channel for further monitoring a quantity of air present in the pumping system.

5. A pumping system according to claim 1, further comprising:

at least one additional pump controlled by the controller, said additional pump including a pump outlet; and a manifold for receiving liquid from pump outlets of the pump and said at least one additional pump for mixing the liquids.

6. A pumping system according to claim 5, further comprising:

a drug supply container, at least one of the pumps being connected to said drug supply container to dispense a drug to the manifold.

7. Apparatus according to claim 1, wherein a volume of the pumping chamber is greater than a volume of a portion of the liquid supply channel between the pump inlet and the liquid supply inlet.

8. A system for providing positive displacement, volumetric liquid control comprising:

a liquid supply channel having it liquid inlet and a liquid outlet;

means for detecting air in liquid within the liquid supply channel; and means for providing bi-directional control of liquid flow within the liquid supply channel between the liquid inlet and the liquid outlet until the quantity of air in liquid within the liquid supply channel corresponds to a predetermined value during priming of the liquid supply channel.

9. A system according to claim 8, wherein the means for providing bi-directional control further includes:

a pump located in the liquid supply channel;

a first valve for regulating liquid flow into the pump; and a second valve for regulating liquid flow out of the pump.

10. A system according to claim 9, wherein said pump includes a pumping chamber having a volume greater than a volume of a portion of the liquid supply channel between a pump inlet and the liquid supply inlet.

11. A system according to claim 9, wherein the detecting means further includes:

a first detector located between the liquid inlet and the first valve; and a second detector located between the second valve and the liquid outlet.

12. A system according to claim 11, wherein the detecting means further includes:

at least one pressure detector for determining whether the quantity of air in liquid in the liquid supply channel exceeds a predetermined threshold.

13. A system according to claim 11, wherein the means for providing bi-directional control further includes:

means for controlling the first and second valves and the pump in response to outputs from the first and second detectors.

14. A system according to claim 8, wherein the bi-directional control means further includes:

means for inhibiting the bi-directional control of liquid flow upon expiration of a predetermined time period.

15. A method for providing positive displacement, volumetric control of liquid comprising the steps of:

establishing a liquid path between a liquid inlet and a liquid outlet;

detecting air in liquid within the liquid supply path during an initial priming of the supply path; and providing bi-direction control of liquid within the liquid supply path until the quantity of air in liquid corresponds to a predetermined value during priming of the liquid supply path.

16. A method according to claim 15, wherein said providing step includes pumping a volume of liquid during a pumping stroke which is greater than a volume of the liquid supply path between a pump inlet and the liquid supply inlet.

17. A method according to claim 15, wherein the step of providing bi-directional control further includes the step of:

detecting the presence of liquid at the liquid outlet.

18. A method according to claim 17, wherein the step of providing bi-directional control further includes the step of:

redirecting liquid flow between the liquid inlet and the liquid outlet when the quantity of air in liquid at the liquid inlet corresponds to the predetermined value.

19. A method according to claim 18, wherein the step of providing bi-directional control further includes the step of:

redirecting liquid flow from the liquid outlet to the liquid inlet when quantity of air in liquid exceeds the predetermined value prior to detecting a set number of pumping strokes.

20. A method according to claim 18, wherein the step of providing bi-directional control further includes the step of:

pumping a predetermined volume of liquid to the liquid outlet upon determining that the quantity of air in liquid at the liquid outlet corresponds to the predetermined value.

21. A method according to claim 20, wherein the step of pumping is performed after the quantity of air in liquid at the liquid outlet corresponds to the predetermined value for a set number of pumping strokes.

22. A method for priming a positive displacement, volumetric pumping system with liquid from a liquid supply comprising the steps of:

pumping liquid from the liquid supply to a pumping system outlet;

detecting air in liquid at the pumping system outlet and directing liquid to flow toward the liquid supply upon detecting presence of liquid at the pumping system outlet;

detecting the quantity of air at a liquid supply inlet, and redirecting liquid flow from the liquid supply to the pumping system outlet when the quantity of air is less than a predetermined value;

continuously directing liquid flow from the liquid supply to the pumping system outlet and detecting the quantity of air at the pumping system outlet; and redirecting liquid flow from the pumping system outlet to the liquid supply inlet if the quantity of air at the pumping system outlet exceeds a predetermined value for a set number of pumping strokes within a predetermined period of time.

23. A method according to claim 22, wherein said pumping step includes pumping a volume of liquid during a pumping stroke which is greater than a volume of a liquid supply channel between a pump inlet and the liquid supply inlet.

24. A method according to claim 22, further comprising the steps of:

disengaging normal air and pressure sensing alarms during said steps of detecting, directing and redirecting.

25. A method according to claim 24, wherein said step of pumping further includes the step of:

prompting a user to confirm that pumping should be initiated.

26. A method according to claim 24, further comprising a step of:

prompting a user to confirm when priming is complete; and subsequently reactivating all air and pressure sensing alarms.

27. A method for providing positive displacement, volumetric control of liquid comprising the steps of:

establishing a liquid supply path between a liquid inlet and a liquid outlet;

detecting air in liquid within the liquid supply path during an initial priming of the liquid supply path; and providing bi-directional control of liquid within the liquid supply path until the quantity of air in liquid corresponds to a predetermined value during priming of the liquid supply path, said step of providing further including a step of pumping a predetermined volume of liquid to the liquid outlet upon determining that the quantity of air in liquid at the liquid outlet corresponds to the predetermined value for a set number of pumping strokes.

* * * * *